United States Patent [19]

Tsuji et al.

[11] Patent Number: 5,087,709
[45] Date of Patent: Feb. 11, 1992

[54] PROCESS FOR THE PREPARATION OF 1α,25-DIHYDROXYVITAMIN $D_2$ AND THE 24-EPIMER THEREOF

[75] Inventors: Masahiro Tsuji; Shinji Yokoyama; Yoji Tachibana, all of Saitama, Japan

[73] Assignee: Nisshin Flour Milling Co., Ltd., Tokyo, Japan

[21] Appl. No.: 333,547

[22] Filed: Apr. 4, 1989

[30] Foreign Application Priority Data

Apr. 11, 1988 [JP] Japan ................................. 63-87269
Dec. 28, 1988 [JP] Japan ................................. 63-329178

[51] Int. Cl.$^5$ .......................... C07J 9/00; C07C 172/00
[52] U.S. Cl. ...................................... 552/541; 552/653
[58] Field of Search ...................... 260/397.2; 544/224; 552/541, 653

[56] References Cited

U.S. PATENT DOCUMENTS 4,717,721 1/1988 DeLuca et al. ...................... 514/157

FOREIGN PATENT DOCUMENTS 0028484 5/1981 European Pat. Off. ......... 260/397.2

OTHER PUBLICATIONS

Sal et al., Chem. Pharm. Bull., 34(11), 4508–4515, 1986.
Cary and Sutherland, Advanced Organic Chemistry, 2nd Ed. (New York, Plenum Press, 1984), pp. 74 to 75.
Sicinski et al., Bioorganic Chemistry, 13, pp. 158–165 (1985).
Baggiolini et al., J. Org. Chem., 51, 3098–3108 (1986).
Yamada et al., Tetrahedron Letters, 25, No. 31, pp. 3347–3350 (1984).
Tachibana, Bull. Chem. Soc. of Jpn. 61, 3915–3918 (1988).
Burton et al., J. Chem. Soc. (C), 1968–1974 (1971).
Morris et al., J. Org. Chem., 46, 3422–3428 (1981).
Kociencki et al., J. Chem. Soc. Perkin I, 829–834 (1978).

Primary Examiner—Robert T. Bond
Assistant Examiner—E. C. Ward
Attorney, Agent, or Firm—Abelman Frayne & Schwab

[57] ABSTRACT

(22E)-5,7,22-Ergostatriene-1α,3β,25-triol and the 24-epimer thereof which are new intermediates for the synthesis of 1α,25-dihydroxyvitamin $D_2$ and the 24-epimer thereof. A new process for the preparation of 1α,25-dihydroxyvitamin $D_2$ and the 24-epimer thereof is also described which comprises irradiation of (22E)-5,7,22-ergostatriene-1α,3β,25-triol or the 24-epimer thereof followed by isomerization.

1 Claim, No Drawings

PROCESS FOR THE PREPARATION OF 1α,25-DIHYDROXYVITAMIN D₂ AND THE 24-EPIMER THEREOF

FIELD OF THE INVENTION

This invention relates to new steroid derivatives which are useful intermediates in the preparation of 1α,25-dihydroxyvitamin D$_2$ or the 24-epimer thereof, and also to a process of preparing the intermediates and 1α,25-dihydroxy vitamin D$_2$ or its 24-epimer.

BACKGROUND OF THE INVENTION

The 1α,25-dihydroxy vitamin D$_2$ is the compound having the highest vitamin activity of the vitamin D$_2$ compounds. Further, the 24-epimer of 1α,25-dihydroxy vitamin D$_2$ is very attractive in recent years from the viewpoint of pharmacological activity.

The processes for the preparation of 1α,25-dihydroxyvitamin D$_2$ are known by the method of H. F. DeLuca et al disclosed in Bioorganic Chemistry, 13, 158 (1985) and Japanese Patent LOP Publn. No. 501261/1985 (WO84/04527) and by the method of E. G. Baggiolini et al disclosed in J. Org. Chem. 51, 3098 (1986).

However, the former method is not suitable for the synthesis of only the end compound, 1α,25-dihydroxyvitamin D$_2$, since a number of isomers are formed and each isomer must be fractionated by high pressure liquid chromatography (HPLC) or the like. Further, the latter method is not satisfactory in an industrial scale, since a large number of process steps are required.

The process for the preparation of the 24-epimer of 1α,25-dihydroxyvitamin D$_2$ is known by the method of H. F. DeLuca et al as described in the above references and by the method of H. F. DeLuca et al disclosed in J. Org. Chem. 53, 3450 (1988) and Tetrahedron Letters, 28, 6129 (1987).

However, the former method is not suitable for the same reasons as mentioned above. Further, the latter method is not satisfactory in an industrial scale, since the yield is low and a starting material is expensive.

Now, we have studied the prior art processes for the preparation of 25-dihydroxyvitamin D$_2$ by irradiation of (22E)-5,7,22-ergostatriene-3β,25-diol followed by isomerization (Tetrahedron Letters, 25, 3347 (1984)) and as a result it was found that a process via new intermediates, (22E)-5,7,22-ergostatriene-1α,3β,25-triol and its 24-epimer can afford the desired 1α,25-dihydroxyvitamin D$_2$ and its 24-epimer in more favorable yields, simpler reaction operation and the like as compared with the above prior art processes.

SUMMARY OF THE INVENTION

An object of the invention is to provide new intermediate compounds, (22E)-5,7,22-ergostatriene-1α,3β,25-triol and the 24-epimer thereof and a process for the preparation thereof.

Another object of the invention is to provide a simpler process for the preparation of 1α,25-dihydroxy vitamin D$_2$ and the 24-epimer thereof.

Other objects, advantages and aspects of this invention will become apparent from the detailed description and claims which follow.

DETAILED DESCRIPTION OF THE INVENTION

The essence of the invention is the discovery that new intermediates, (22E)-5,7,22-ergostatriene-1α,3β,25-triol (Ia) and the 24-epimer (Ib) in the synthesis of 1α,25-dihydroxyvitamin D$_2$ (IIa) and the 24-epimer (IIb) are prepared by reaction of the corresponding 1α,3β-diol diacetate (III) with 4-phenyl-1,2,4-triazoline-3,5-dione to yield a Diels-Alder adduct (IV), oxidation of the compound (IV) with ozone followed by reductive workup to afford an aldehyde compound (V), reaction of a sulfone compound (A) followed by reductive elimination to give a (22E)-olefin compound (VII), removal of a tetrahydropyranyl group which protects the 25-hydroxy group of the compound (VII) to afford a triol compound (VIII) and reduction of the compound (VIII) to remove the protecting group in the 5,7-diene.

The processes of the invention are for example illustrated by the following reaction scheme I which includes the synthetic route starting from the compound (III) via the intermediates, (22E)-5,7,22-ergostatriene-1α,3β,25-triol (Ia) and the 24-epimer (Ib), leading to a desired final product, 1α,25-dihydroxyvitamin D$_2$ (IIa) and the 24-epimer (IIb).

Scheme I

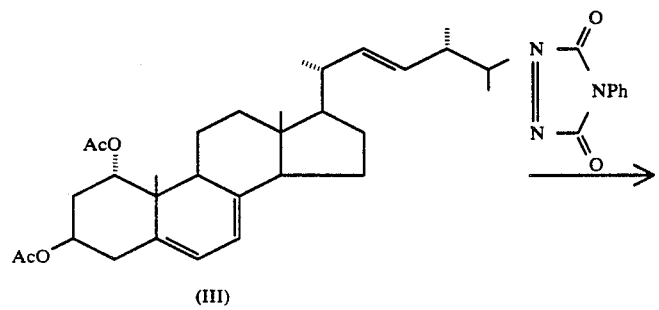

(III)

Scheme I
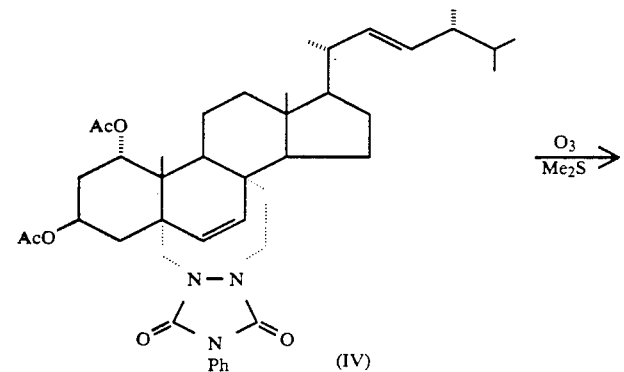
(IV)
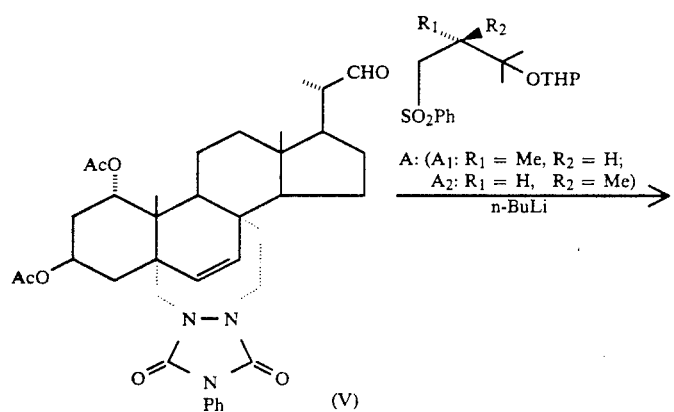
A: (A₁: $R_1$ = Me, $R_2$ = H;
A₂: $R_1$ = H, $R_2$ = Me)
n-BuLi
(V)
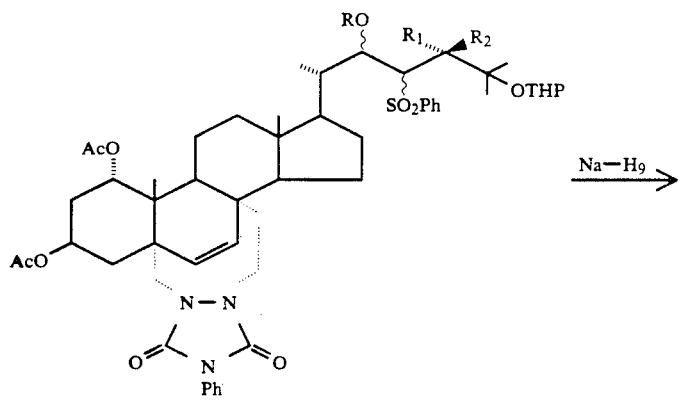
Na—H₉
(VI): (VIa: R = H, $R_1$ = Me, $R_2$ = H;
VIb: R = H, $R_1$ = H, $R_2$ = Me)
(VI'): (VI'a: R = Ac, $R_1$ = Me, $R_2$ = H;
VI'b: R = Ac, $R_1$ = H, $R_2$ = Me)

Scheme I
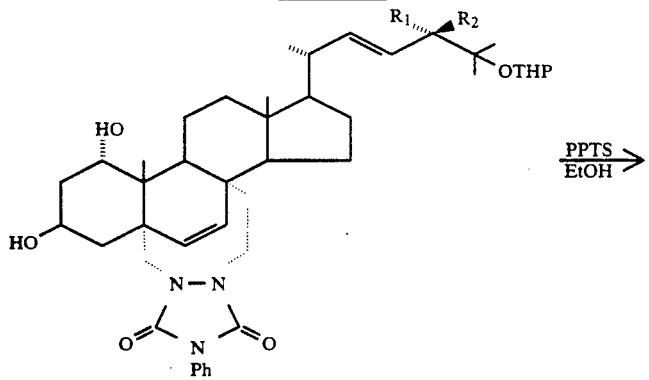
(VII): (VIIa: R₁ = Me, R₂ = H;
VIIb: R₁ = H, R₂ = Me)
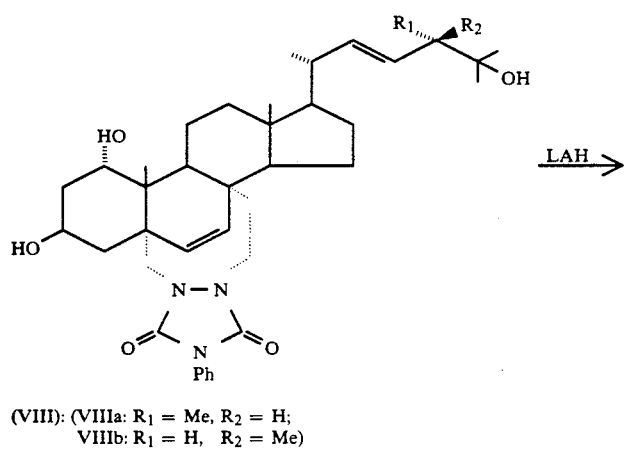
(VIII): (VIIIa: R₁ = Me, R₂ = H;
VIIIb: R₁ = H, R₂ = Me)
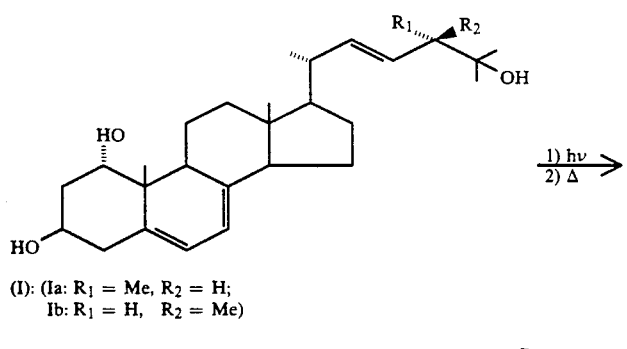
(I): (Ia: R₁ = Me, R₂ = H;
Ib: R₁ = H, R₂ = Me)
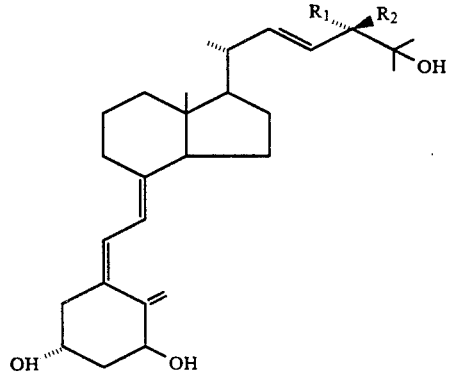
(II): (IIa: R₁ = Me, R₂ = H;
IIb: R₁ = H, R₂ = Me)

In the scheme I, (22E)-5,7,22-ergostatriene-1α,3β-diol diacetate of formula (III) used for a starting material can be prepared from ergosterol in accordance with the method mentioned by H. F. DeLuca et al in Steroids, 30, 671 (1977) or by Y. Tachibana in Bull. Chem. Soc. Jpn. 61, 3915 (1988). The synthetic route is shown by the following reaction schemes II-a and II-b.
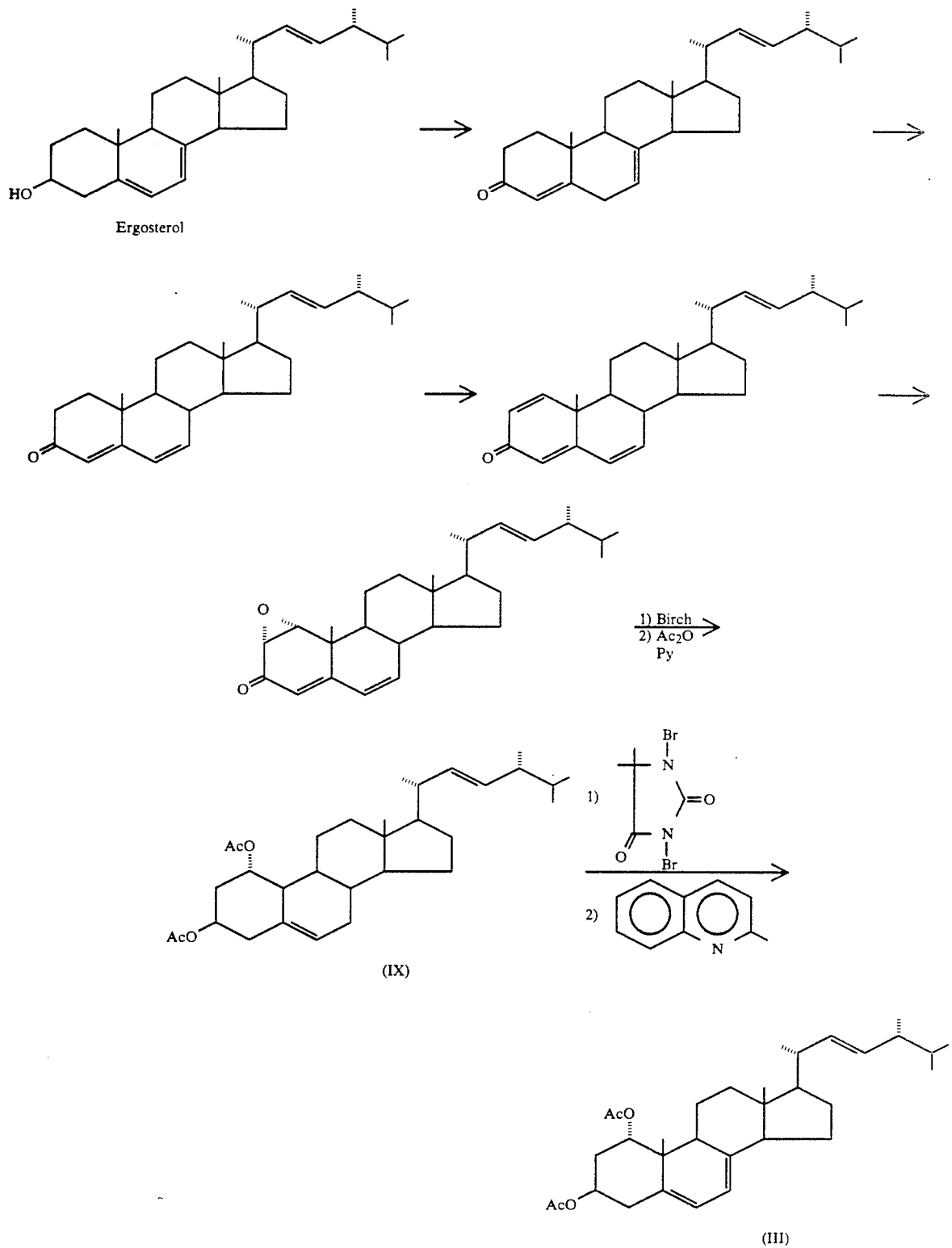

Scheme II-b
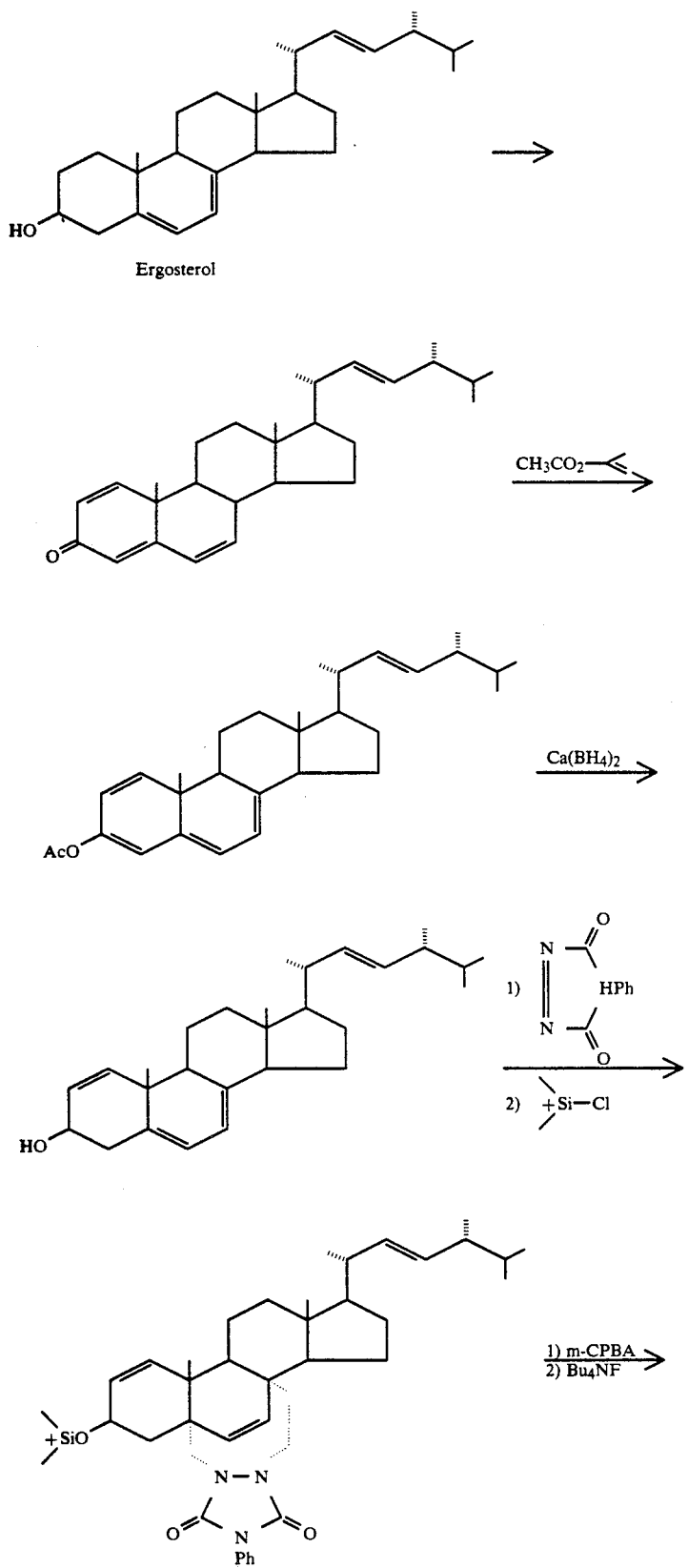

Scheme II-b

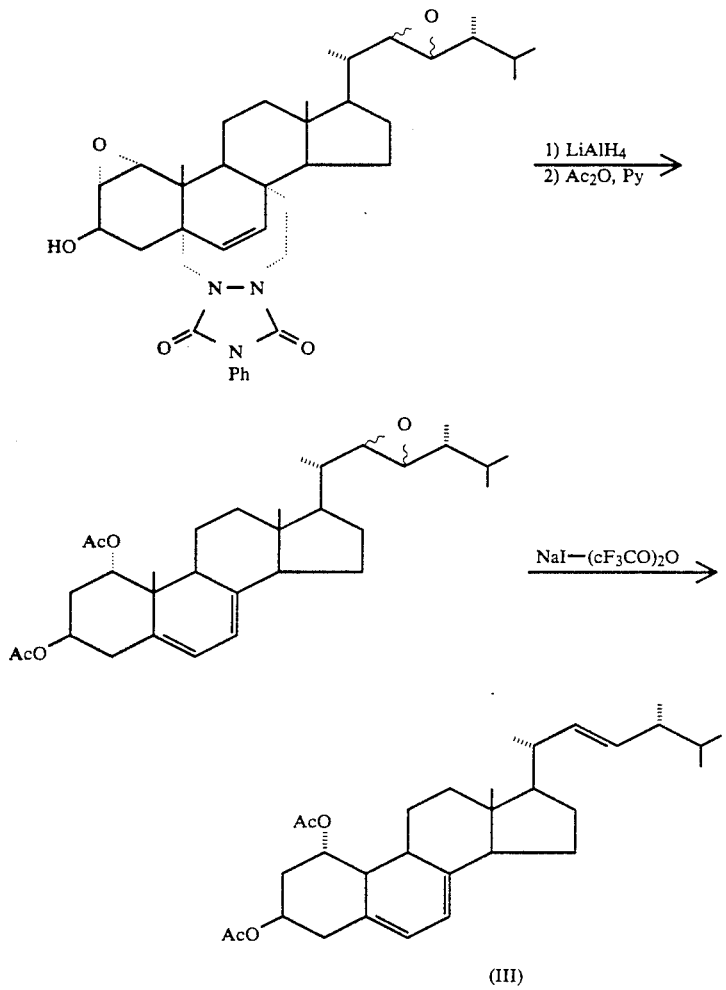

According to the reaction scheme II-a, a starting material, (22E)-5,7,22-ergostatriene-1α,3β-diol diacetate of formula (III) is prepared from a compound of formula (IX), with the simultaneous formation of the 4,6-diene which requires further purification to recover only the 5,7-diene of formula (III) in pure form. The purification methods used in this case include silica gel chromatography, recrystallization and the like.

As illustrated in the reaction scheme I, the compound of formula (III) is reacted with 4-phenyl-1,2,4-triazoline-3,5-dione to afford a Diels-Alder adduct of formula (IV). This reaction is carried out at a temperature between 0° C. and room temperature in an ordinary solvent, e.g. hydrocarbon solvents such as hexane, benzene and toluene, ketone solvents such as acetone and methyl ethyl ketone and halogen solvents such as chloroform and methylene chloride. In the reaction, 4-phenyl-1,2,4-triazoline-3,5-dione is used in the range beyond the equimolecular amount of the compound of formula (III), preferably in the range of 1.0 to 1.5 moles per mole of the compound (III).

Further, 4-phenyl-1,2,4-triazoline-3,5-dione reacts with only the 5,7-diene and does not react with the 4,6-diene, both dienes forming during the reaction course from the compound (IX) to the compound (III). In such situation, the compound (III) does not require any purification for further use, after the reaction for the preparation of the compound (III) from the compound (IX).

After the 5,7-diene of formula (III) is protected with a triazoline compound, the compound of formula (IV) is subjected to oxidation with ozone followed by reductive workup to give an aldehyde of formula (V).

The reaction to obtain the aldehyde of formula (V) can be carried out in accordance with the methods taught by D. H. R. Barton et al. (J. Chem. Soc., (c), 1968 (1971)) or by D. H. Williams et al. (J. Org. Chem, 46, 3422 (1981)), and these methods may eliminate the epimerization on the 20-carbon atom of the compound (V).

The oxidation with ozone is carried out at a temperature between −60° C. and −78° C. in methylene chloride containing 1% pyridine by blowing through the compound of formula (IV) an ozone in an equimolecular amount or a slightly excess molar amount based on the compound (IV). The ozonide thus prepared is then subjected to reduction reaction with an excess amount of the reducing agents such as dimethyl sulfide, hexamethyl phosphorous triamide and the like to give the aldehyde of formula (V). This reaction is carried out at the same temperature as used for the ozone blowing.

The reaction of the aldehyde (V) with a sulfone of formula (A) followed by reductive elimination affords a 22, 23-trans olefin of formula (VII). This reaction can be carried out in accordance with the process taught by P. J. Kocienski, B. Lythgoe, et al. in J. Chem. Soc. Perkin I, 829 (1978). More specifically, the aldehyde of formula (V) is reacted with an optically active sulfone of formula (A) in the presence of a strong organic base to give a β-hydroxy sulfone of formula (VI) as shown in the scheme I. The compound (VIa) is subjected, as such or after conversion to β-acetoxy sulfone of formula (VI'), to reductive elimination reaction with sodium amalgam to give 22, 23-trans olefin (22E-olefin) of formula (VII). The reaction of the aldehyde (V) with the sulfone (A) is carried out forming an anion of the sulfone (A) with a strong organic base such as n-butyl lithium, lithium diisopropylamide (LDA) and the like in tetrahydrofuran at a temperature between −60° C. and −78° C., followed by the addition of the aldehyde (V). The amounts of the sulfone (A) and the organic base used are in the range of 1.0 to 5.0 moles, preferably 1.2 to 2.0 moles per mole of the aldehyde (V). A β-acetoxy sulfone of formula (VI') is obtained by adding acetic anhydride to the reaction mixture of β-hydroxy sulfone of formula (VI). The compound of formula (VI) or (VI') is treated with an excess amount of sodium amalgam in a mixed solution of ethyl acetate and methanol or in methanol saturated with Na₂HPO₄. The reaction is conducted at a temperature between −40° C. and room temperature, preferably between −20° C. and room temperature. During the course of this reaction, the acetyl groups protecting the hydroxy groups at the 1- and 3-position of the compounds (VI) and (VI') are eliminated.

Further, an optically active sulfone of formula (A) can be prepared from a commercially available optically active methyl (S)-(+)-3-hydroxy-2-methylpropionate and the (R)-(−)-form thereof as shown in the scheme III.

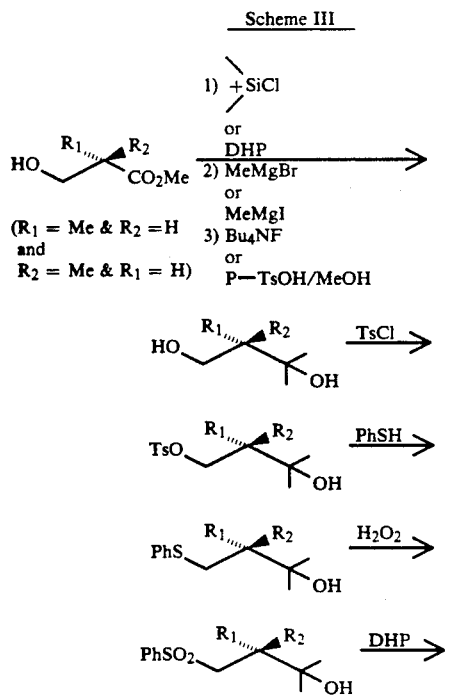

(A): (A₁: R₁ = Me, R₂ = H;
A₂: R₁ = H, R₂ = Me)

Removal of the tetrahydropyranyl group protecting the 25-hydroxy group from the compound (VII) affords a triol of formula (VIII) wherein the 5,7-diene is protected. This removal of the tetrahydropyranyl group is carried out in a conventional manner under acidic conditions. Thus the reaction is carried out by treatment with p-toluenesulfonic acid, pyridinium p-toluenesulfonate, an acidic ion exchange resin, e.g. Amberlist 15 ® (Rohm & Haas Company) in methanol or ethanol and the like under acidic conditions such as acetic acid/water, acetic acid/water/tetrahydrofuran. Preferably, this reaction is carried out in ethanol at a temperature between 45° C. and 60° C. using pyridinium p-toluenesulfonate in the amount of 0.01 to 0.1 moles per mole of the compound (VII).

The compound of formula (VIII) is subjected to reduction to remove the protecting group for the 5,7-diene, affording (22E)-5,7,22-ergostatriene-1α,3β,25-triol and its 24-epimer of formula (I). This reaction is performed in a conventional manner. Thus, the reaction is carried out in tetrahydrofuran at its boiling point using an excess amount of lithium aluminum hydride (LiAlH₄) for the compound of formula (VIII).

(22E)-5,7,22-Ergostatriene-1α,3β,25-triol and its 24-epimer of formula (I) can be converted into 1α,25-dihydroxyvitamin D₂ and its 24-epimer of formula (II) by a general procedure for the synthesis of vitamin D from the 5,7-diene. More particularly, (22E)-5,7,22-ergostatriene-1α,3β,25-triol and its 24-epimer of formula (I) in tetrahydrofuran/ether were respectively irradiated to afford a previtamin D. The previtamin D was isomerized by heating in a suitable solvent, e.g. ethanol. Purification of the resulting products by chromatography and recrystallization affords 1α,25-dihydroxyvitamin D₂ and the 24-epimer thereof.

According to the process of the invention, the desired 1α,25-dihydroxyvitamin D₂ and the 24-epimer thereof can be prepared in easy way without requiring the separation of isomers and through a relatively small number of the process steps.

The invention is further illustrated by the following non-limitative examples.

EXAMPLE 1

(22E)-5α,8α-(4-phenyl-1,2-urazolo)-6,22-ergostadiene-1α,3β-diol diacetate (IV)

1,3-Dibromo-5,5-dimethylhydantoin (3.45 g, 12 mmol), sodium bicarbonate (400 mg) and lauroyl peroxide (50 mg) were added to a solution of (22E)-5,22-ergostadiene-1α,3β-diol diacetate (IX) (10.0 g, 20 mmol) in hexane (150 ml). The reaction solution was stirred under reflux for 25 minutes. After cooling, the crystals were separated by filtration from the reaction mixture and hexane was distilled off from a filtrate. The residue was dissolved in butyl acetate (80 ml) and added dropwise to a solution of quinaldine (14.3 g, 100 mmol) in butyl acetate (70 ml) with stirring under reflux. The mixture was further refluxed for 40 minutes. After cooling, the reaction mixture was washed successively with 2N hydrochloric acid, water, saturated sodium bicarbonate solution and saturated sodium chloride solution, and dried over anhydrous magnesium sulfate. After filtration, the filtrate was concentrated to give a crude (22E)-5,7,22-ergostatriene-1α,3β-diol diacetate (III) which was dissolved in chloroform (50 ml) and a solution of 4-phenyl-1,2,4-triazoline-3,5-dione (2.26 g, 13 mmol) in acetone (40 ml) was added dropwise with stirring at room temperature. After concentration of the reaction mixture, the resulting residue was purified by silica gel column chromatography eluting with 2/1 hexane/ethyl acetate to give 3.5 g of the foamy title compound (IV).

$\alpha_{D25} -139°$ (c=1.09, CHCl$_3$).

NMR (CDCl$_3$): δ0.79 and 0.82 (6H, each d, J=3.7 Hz, 26-H$_3$ and 27-H$_3$). 0.84 (3H, s, 18-H$_3$), 0.89 (3H, d, J=6.8 Hz, 28-H$_3$), 1.02 (3H, d, J=6.6 Hz, 21-H$_3$), 1.06 (3H, s, 19-H$_3$), $$\underset{2.01(3H,\ s,\ -CCH_3),}{\overset{O}{\underset{\|}{C}}}\ \underset{2.03(3H,\ s,\ -CCH_3),}{\overset{O}{\underset{\|}{C}}}$$

3.25 (1H, dd, J$_1$=5.6 Hz, J$_2$=13.7 Hz, 9-H), 5.11 (1H, m, 1-H), 5.20 (2H, m, 22-H and 23-H), 5.89 (1H, m, 3-H), 6.33 and 6.45 (2H, AB$_q$, J=8.3 Hz, 6-H and 7-H), 7.24-7.51 (5H, m, -Ar-H).

IR (KBr): 1750, 1700, 1600, 1505, 1395, 1240, 1030 cm$^{-1}$.

mass spectrum: m/e 671(M$^+$, 0.3), 496(0.4), 436(8), 376(100), 251(28), 209(23), 155(34);

EXAMPLE 2

22-Oxo-5α,8α-(4-phenyl-1,2-urazolo)-23,24-dinor-6-chlorene-1α,3β-diol diacetate (V)

(22E)-5α,8α-(4-phenyl-1,2-urazolo)-6,22-ergostadiene-1α,3α-diol diacetate (Diels-Alder adduct (IV)) (10.00 g, 14.9 mmol) was dissolved in a mixed solution of 1% pyridine and methylene chloride (400 ml). Ozone (0.07 mmol/min) was bubbled into the solution with stirring at −65° C. for 4.5 hrs. After ozone was expelled by passing an argon gas through the reaction solution, dimethyl sulfide (20 ml) was added dropwise at −65° C. over a period of 15 minutes. The solution was stirred at the same temperature for one hour, and gradually returned to room temperature over a period of one hour. The reaction mixture was washed with 2% hydrochloric acid (400 ml), then saturated sodium chloride solution and dried over anhydrous magnesium sulfate. After filtration, methylene chloride was distilled off and the residue was purified by silica gel column chromatography eluting with 1/1 hexane/ethyl acetate to give 5.99 g of the title compound (V). Recrystallization from benzene afforded 4.40 g of the compound (V) as crystals.
m.p. 191°-193° C.

$\alpha_D^{25} -131°$ (c=1.06, CHCl$_3$).

NMR (CDCl$_3$): δ 0.87 (3H, s, 18-H$_3$), 1.07 (3H, s, 19-H$_3$), 1.14 (3H, d, J=6.8 Hz, 21-H$_3$), $$\underset{2.01(3H,\ s,\ -CCH_3),}{\overset{O}{\underset{\|}{C}}}\ \underset{2.04(3H,\ s,\ -CCH_3),}{\overset{O}{\underset{\|}{C}}}$$

3.26 (1H, dd, J$_1$=5.4 Hz, J$_2$=14.2 Hz, 9-H), 5.12 (1H, m, 1-H), 5.88 (1H, m, 3-H), 6.36 and 6.44 (2H, ABq, J=8.3Hz, 6-H and 7-H), 7.26-7.51 (5H, m, -Ar-H), 9.55 (1H, d, J=3.4 Hz, 22-H).

IR (KBr): 2720, 1740, 1685, 1605, 1505, 1405, 1370, 1250, 1230, 1035 cm$^{-1}$.

mass spectrum: m/e 603(M$^+$, 0.3), 428(0.3), 368(11), 308(100), 235(20), 177(20), 141(57).

EXAMPLE 3

(22E)-5α,8α-(4-phenyl-1,2-urazolo)-25-(2'-tetrahydropyranyloxy)-6,22-ergostadiene-1α,3β-diol (VIIa)

To a solution of the sulfone (A$_1$) (1.70 g, 5.2 mmol) in anhydrous tetrahydrofuran (60 ml) was added dropwise n-butyllithium (1.5N hexane solution, 3.5 ml, 5.2 mmol) at −65° C. under argon atmosphere and the solution was stirred at the same temperature for 30 minutes. Then, a solution of 22-oxo-5α,8α-(4-phenyl-1,2-urazolo)-23,24-dinor-6-cholene-1α,3β-diol diacetate (aldehyde (V)) (2.40 g, 4.0 mmol) in anhydrous tetrahydrofuran (25 ml) was added dropwise at the same temperature and the solution was further stirred for 30 minutes at that temperature. Thereafter, a saturated ammonium chloride solution (1 ml) was added dropwise and the reaction mixture was returned to room temperature. The reaction mixture was poured into a saturated ammonium chloride solution and extracted with ethyl acetate. The ethyl acetate layer was washed with a saturated sodium chloride solution, dried over anhydrous magnesium sulfate. After filtration, ethyl acetate was distilled off and the residue (containing β-hydroxysulfone (VIa)) was dissolved in methanol (330 ml) saturated with Na$_2$HPO$_4$, to which was added sodium amalgam (5%, 18.3 g) and the mixture was stirred at 0° C. for 15 hrs and then at room temperature for 3 hrs. The supernatant was taken and methanol was distilled off and the residue to which was added water was extracted with ethyl acetate. The ethyl acetate layer was washed with a saturated sodium chloride solution and dried over anhydrous magnesium sulfate. After filtration, ethyl acetate was distilled off and the residue was purified by silica gel column chromatography eluting with ¼ hexane/ethyl acetate to give 0.87 g of the title compound (VII).

NMR (CDCl$_3$): δ

3.48(1H, m, —O—[tetrahydropyranyl ring with H, H]), 3.69 (1H, m, 1-H), 3.95(1H, m, —O—[tetrahydropyranyl]), 4.78(1H, m, —O—[tetrahydropyranyl]), 4.85 (1H, m, 3-H), 5.15-5.42 (2H, m, 22-H and 23-H), 6.18 and 6.34 (2H, AB$_q$, J=8.3 Hz, 6=H and 7-H), 7.2-7.4 (5H, m, -Ar-H).

IR (KBr): 3420, 1745, 1685, 1600, 1505, 1405, 1315, 1130, 1025, 980 cm$^{-1}$.

mass spectrum: m/e 512 (M$^+$- triazoline, 0.3), 428(3), 410(22), 324(3), 251(5), 177(22), 119(28), 85(100), 59(94).

EXAMPLE 4

(22E)-5,7,22-ergostatriene-1α,3β,25-triol (Ia)

To a solution of (22E)-5α,8α-(4-phenyl-1,2-urazolo)-25-(2'-tetrahydropyranyloxy)-6,22-ergostadiene-1α,3β-diol (VIIa) (0.84 g, 1.2 mmol) in 95% ethanol (6 ml) was added pyridinium p-toluenesulfonate (15 mg) and the mixture was stirred at 50° C. for one hour. From the reaction mixture was distilled away ethanol and the residue to which was added a saturated sodium chloride solution was extracted with ethyl acetate. The ethyl acetate layer was dried over anhydrous magnesium sulfate. After filtration, ethyl acetate was distilled off to give a crude compound (VIII) as the residue. The product was used for the next step without further purification, but a sample for analysis was prepared by recrystallization from ethanol-ether (the crystals containing ¼ Et₂O).

m.p. 209°-212° C.

$\alpha_D^{25}$ −86.4° (c=0.22, CHCl₃).

NMR (CDCl₃): δ 0.84 (3H, s, 18-H₃), 0.93 (3H, s, 19-H₃), 0.98 (3H, d, J=7.1 Hz, 28-H₃), 1.05 (3H, d, J=6.6 Hz, 21-H₃), 1.13 and 1.16 (6H, each s, 26H₃ and 27-H₃), 1.21 (t, J=7.1 Hz, Et₂O), 3.15 (1H, dd, J₁=7.1 Hz, J₂=14 Hz, 9-H), 3.48 (q, J=7.1 Hz, Et₂O), 3.85 (1H, m, 1-H), 4.90 (1H, m, 3-H), 5.35 (2H, m, 22-H and 23-H), 6.26 and 6.41 (2H, AB$_q$, J=8.3 Hz, 6-H and 7-H), 7.30–7.45 (5H, m, -Ar-H).

IR (KBr): 3530, 3470, 1745, 1680, 1505, 1415, 1150, 1035 cm⁻¹.

mass spectrum: m/e 428(M⁺-triazoline, 18), 350(15), 324(25), 251(15), 177(90), 119(100).

The above residue containing the compound (VIIIa) was dissolved in anhydrous tetrahydrofuran (80 ml) and lithium aluminum hydride (0.73 g) was added to the solution and the mixture was stirred under reflux for 1.5 hrs. To the ice-cooled mixture was added successively water (0.7 ml), 10% sodium hydroxide solution (0.7 ml) and water (2.1 ml). The mixture was stirred at room temperature for 30 minutes and dried over anhydrous magnesium sulfate. After filtration, tetrahydrofuran was distilled off and the residue was recrystallized from ethanol to give 0.28 g of the title compound (Ia).

m.p. 222°-224° C.

$\alpha_D^{25}$ −55° (c=0.12, MeOH).

NMR (CDCl₃): δ 0.64 (3H, s, 18-H₃), 0.95 (3H, s, 19-H₃), 100 (3H, d, J=7.1 Hz, 28-H₃), 1.05(3H, d, J=6.8 Hz, 21-H₃), 1.13 and 1.17 (6H each s, 26-H₃ and 27-H₃), 3.77 (1H, m, 1-H), 4.04 (1H, m, 3-H), 5.35 (3H, m, 22-H and 23-H and 7-H), 5.73 (1H, m, 6-H).

IR (KBr): 3520, 3350, 1655, 1610, 1465, 1370, 1135, 1070, 975 cm⁻¹.

mass spectrum: m/e 428(M³⁰ , 4), 353(2), 312(2), 251(5), 225(5), 145(8), 81(15), 59(100).

UV (EtOH): λ$_{max}$282 nm.

EXAMPLE 5

1α,25-Dihydroxyvitamin D₂ (IIa)

(22E)-5,7,22-Ergostatriene-1α,3β,25-triol (Ia) (100 mg, 0.23 mmol) was dissolved in a mixed solution of ether (950 ml) and tetrahydrofuran (50 ml), and the solution was irradiated with high pressure mercury lamp using an 1.5% aqueous potassium nitrate solution as a filter with water cooling in a nitrogen stream for 3 minutes. From the reaction solution was distilled off the solvent and the residue containing previtamin D was dissolved in ethanol (30 ml) and the solution was refluxed for one hour. After distilling off ethanol, the residue was purified by high pressure liquid chromatography (HPLC) (column: LiChrosorb ® Si60 (7 μm), φ25×250 mm, Merck Co., Ltd.; column effluent: 4% methanol-methylene chloride; flow rate: 8.0 ml/min; detected at 264 nm) to give 22 mg of the title compound (IIa) which was recrystallized from hexane-ether. m.p. 168°–170° C.

$\alpha_D^{25}$ +48° (c=0.07, EtOH).

NMR (CDCl₃): δ 0.56 (3H, s, 18-H₃), 1.00 (3H, d, J=6.8 Hz, 28-H₃), 1.04 (3H, d, J=6.8 Hz, 21-H₃), 1.13 and 1.17 (6H, each s, 26-H₃ and 27-H₃), 4.23 (1H, m, 3-H), 4.42 (1H, m 1-H), 5.00 (1H, narrow m, 19-H), 5.32 (3H, m, 19-H and 22-H and 23-H), 6.01 (1H, d, J=10.6 Hz, 7-H), 6.38 (1H, d, J=10.6 Hz, 6-H).

IR (KBr): 3400, 1640, 1460, 1380, 1370, 1350, 1300, 1265, 1220, 1140, 1055, 975 cm⁻¹.

mass spectrum: m/e 428(M³⁰ , 5), 410(9), 392(12), 352(6), 269(10), 197(15), 152(23), 134(100).

UV (EtOH): λ$_{max}$265.5 nm

EXAMPLE 6

(24R, 22E)-5α,8α-(4-Phenyl-1,2-urazolo)-25-tetrahydropyranyloxy-6,22-ergostadiene-1α,3β-diol (VIIb)

to a solution of the sulfone (A₂) (1.62 g, 5.0 mmol) in anhydrous tetrahydrofuran (20 ml) was added dropwise n-butyllithium (1.5N hexane solution, 3.3 ml, 5.0 mmol) at −70° C. under argon atmosphere and the solution was stirred at the same temperature for 30 minutes. Then, a solution of 22-oxo-5α,8α-(4-phenyl-1,2-urazolo)-23,24-dinor-6-cholene-1α,3β-diol diacetate (aldehyde (V)) (1.50 g, 2.5 mmol) in anhydrous tetrahydrofuran (15 ml) was added dropwise at the same temperature and the mixture was further stirred for 30 minutes at that temperature. Thereafter, a saturated ammonium chloride solution (1 ml) was added dropwise and the reaction mixture was returned to room temperature. The reaction mixture was poured into a saturated ammonium chloride solution and extracted with ethyl acetate. The ethyl acetate layer was washed with a saturated sodium chloride solution, dried over anhydrous magnesium sulfate. After filtration, ethyl acetate was distilled off and the residue (containing β-hydroxysulfone (VIb) was dissolved in methanol (200 ml) saturated with Na₂HPO₄, to which was added sodium amalgam (5%, 11.4 g) and the mixture was stirred at 0° C. for 18 hrs and then at room temperature for 4 hrs. The supernatant was taken and methanol was distilled off and the residue to which was added water was extracted with ethyl acetate. The ethyl acetate layer was washed with a saturated sodium chloride solution and dried over anhydrous magnesium sulfate. After filtration, ethyl acetate was distilled off and the residue was purified by silica gel column chromatography eluting with ¼ hexane/ethyl acetate to give 0.46 g of the title compound (VIIb).

NMR (CDCl₃): δ

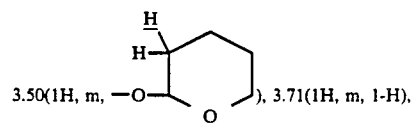

3.90(1H, m, —O—[structure]), 4.75(1H, m, —O—[structure]), 4.85 (1H, m, 3-H), 5.15–5.40 (2H, m, 22-H and 23-H), 6.19 and 6.35 (2H, AB$_q$, J=8.3 Hz, 6-H and 7-H), 7.2–7.4 (5H, m, -Ar-H).

IR (KBr): 3430, 1750, 1690, 1605, 1505, 1410, 1310, 1135, 1030, 985 cm$^{-1}$.

mass spectrum: m/e 428 (M$^{30}$-triazoline-diahydropyran, 10), 410(7), 350(12), 177(40), 119(100).

EXAMPLE 7

(24R, 22E)-5,7,22-Ergostatriene-1α,3β,25-triol (Ib)

To a solution of (24R,22E)-5α,8α-(4-phenyl-1,2-urazolo)-25-tetrahydropyranyloxy-6,22-ergostadiene-1α,3β-diol (VIIb) (0.87 g, 1.3 mmol) in 95% ethanol (6 ml) was added pyridinium p-toluenesulfonate (15 mg) and the mixture was stirred at 50° C. for one hour. From the reaction mixture was distilled away ethanol and the residue to which was added a saturated sodium chloride solution was extracted with ethyl acetate. The ethyl acetate layer was dried over anhydrous magnesium sulfate. After filtration, ethyl acetate was distilled off to give a crude compound (VIIIb) as the residue. The product was used for the next step without further purification, but a sample for analysis was prepared by recrystallization from ethanol-ether (the crystals containing ¼ Et$_2$O).

m.p. 212°–215° C.

$\alpha_D^{25}$ −95.6° (c=0.25, CHCl$_3$).

NMR (CDCl$_3$): δ 0.83 (3H, s, 18-H$_3$), 0.98 (3H, d, J=7.1 Hz, 28-H$_3$), 1.04 (3H, d, J=6.4 Hz, 21-H$_3$), 1.12 and 1.15 (6H, each s, 26-H$_3$ and 27-H$_3$), 1.21 (t, J=7.1 Hz, Et$_2$O), 3.14 (1H, dd, J$_1$=4.4 Hz, J$_2$=13.7 Hz, 9-H), 3.48 (q, J=7.1 Hz, Et$_2$O), 3,83 (1H, m, 1-H), 4.90 (1H, m, 3-H), 5.32 (2H, m, 22-H and 23-H), 6.25 and 6.40 (2H, AB$_q$, J=8.1 Hz, 6-H and 7-H), 7.30–7.45 (5H, m, -Ar-H).

IR (KBr): 3530, 3450, 1745, 1680, 1505, 1420, 1155, 1035 cm$^{-1}$.

mass spectrum: m/e 428(M$^+$-triazoline, 22), 350(16), 324(48), 251(20), 177(75), 119(110).

The above residue containing the compound (VIIIb) was dissolved in anhydrous tetrahydrofuran (70 ml) and lithium aluminum hydride (0.65 g) was added to the solution and the mixture was stirred under reflux for one hour. To the ice-cooled mixture was added successively water (0.7 ml), 10% sodium hydroxide solution (0.7 ml) and water (2.1 ml). The mixture was stirred at room temperature for 30 minutes and dried over anhydrous magnesium sulfate. After filtration, tetrahydrofuran was distilled off and the residue was recrystallized from ethanol to give 0.31 g of the title compound (Ib).

m.p. 214°–217° C.

$\alpha_D^{24}$ −16.2° (c=0.14, MeOH).

NMR (CDCl$_3$): δ 0.65 (3H, s, 18-H$_3$), 0.95 (3H, s, 19-H$_3$), 0.99 (3H, d, J=6.8 Hz, 28-H$_3$), 1.05 (3H, d, J=6.8 Hz, 21-H$_3$), 1.13 and 1.17 (6H, each s, 26-H$_3$ and 27-H$_3$), 3.77 (1H, m, 1-H), 4.08 (1H, m, 3-H), 5.35 (3H, m, 7-H and 22-H and 23H), 5.74 (1H, m, 6-H).

IR (KBr): 3510, 3360, 1660, 1610, 1465, 1385, 1145, 1075,, 970 cm$^{-1}$.

mass spectrum: m/e 428(M$^+$, 42), 251(60), 225(62), 157(100), 145(80).

UV (EtOH): λ$_{max}$282 nm.

EXAMPLE 8

(24R)-1α,25-Dihydroxy vitamin D$_2$ (IIb)

(24R,22E)-5,7,22-Ergostatrien-1α,3β,25-triol (Ib) (100 mg, 0.23 mmol) was dissolved in a mixed solution of ether (950 ml) and tetrahydrofuran (50 ml), and the solution was irradiated with high pressure mercury lamp using an 1.5% aqueous potassium nitrate solution as a filter with water cooling in a nitrogen stream for 3 minutes. The residue obtained by distilling off the solvent from the reaction solution was purified by HPLC (column: Lichrosorb ® Si60 (7 μm), φ25×250 mm, Merck Co., Ltd.; column effluent: 5% methanol/methylene chloride; flow rate: 8.0 ml/min; detected at 265 nm) to give 28 mg of the previtamin D.

NMR (CDCl$_3$): δ 0.72 (3H, s, 18-H$_3$), 0.99 (3H, d, J=6.8 Hz, 28-H$_3$), 1.05 (3H, d, J=6.6 Hz, 21-H$_3$), 1.13 and 1.17 (6H, each s, 26-H$_3$ and 27-H$_3$), 1.76 (3H, s, 19-H$_3$), 4.05 (1H, m, 3-H), 4.19 (1H, m, 1-H), 5.31 (2H, m, 22-H and 23H), 5.51 (1H, m, 9H), 5.76 and 5.92 (2H, AB$_q$, J=12.9 Hz, 6-H and 7-H).

The previtamin D as prepared above was dissolved in ethanol (15 ml) and refluxed for one hour. The reside obtained by distilling off ethanol was purified by HPLC (column: Lichrosorb ® Si60 (7 μm), φ25×250 mm, Merck Co., Ltd.; column effluent: 5% methanol/methylene chloride; flow rate: 7.0 ml/min; detected at 265 nm) to give 11.8 mg of the title compound (IIb). The compound was recrystallized from hexane/methylene chloride.

m.p. 150°–152° C.

$\alpha_D^{23}$ +74° (c=0.16, EtOH).

NMR (CDCl$_3$): δ 0.56 (3H, s, 18-H$_3$), 0.99 (3H, d, J=6.8 Hz, 28-H$_3$), 1.03 (3H, d, J=6.6 Hz, 21-H$_3$), 1.12 and 1.17 (6H, each s, 26-H$_3$ and 27-H$_3$), 4.22 (1H, m, 3-H), 4.42 (1H, m, 1-H), 4.99 (1H, narrow m, 19-H), 5.32 (3H, m, 19-H and 22-H and 23-H), 6.01 (1H, d, J=11.2 Hz, 7-H), 6.37 (1H, d, J=11.2 Hz, 6-H).

mass spectrum: m/e 428(M$^{30}$, 6), 410(7), 392(10), 352(5), 334(6), 269(9), 251(10), 134(100), 105(46).

UV (EtOH): λ$_{max}$265 nm.

What is claimed is:

1. A process of preparing (22E)-5,7,22-ergostatriene-1α,3β,25-triol or its 24-epimer thereof of formula (I)

[structure (I)]

wherein R$_2$ is H when R$_1$ is CH$_3$ (24 S form) and R$_1$ is H when R$_2$ is CH$_3$ (24 R form) which comprises reacting (22E)-5,7,22-ergostatriene-1α,3β-diol diacetate with 4-phenyl-1,2,4-triazoline-3,5-dione to form a Diels-Alder adduct of formula (IV),

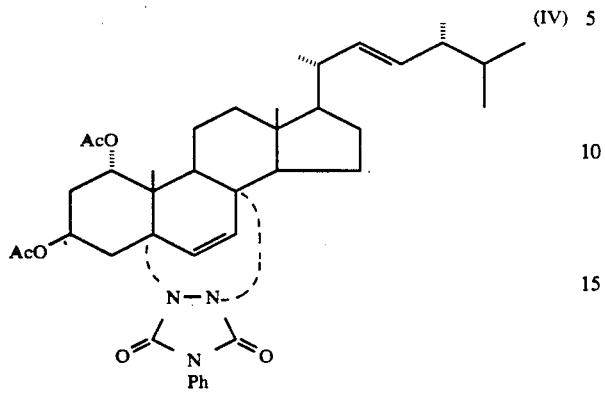

subjecting the Diels-Alder adduct (IV) to oxidation with ozone followed by reductive workup to afford an aldehyde compound of formula (V),

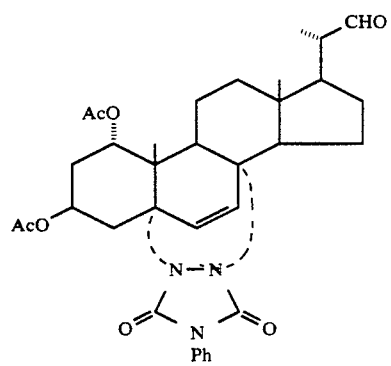

reacting the aldehyde compound (V) with a sulfone compound of formula (A)

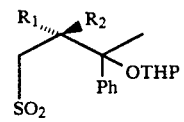

wherein $R_1$ and $R_2$ are as defined above, followed by reductive elimination to give an (22E)-olefin compound of formula (VII)

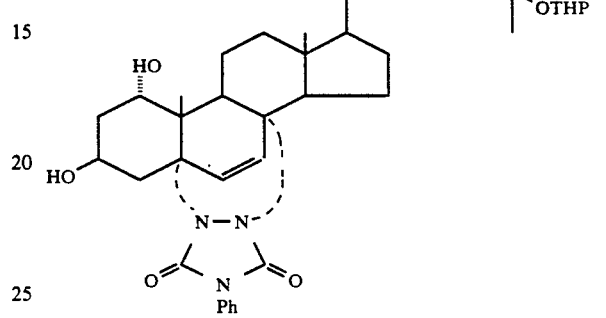

wherein $R_1$ and $R_2$ are as defined above, removing the tetrahydropyranyl group which protects the 25-hydroxy group of the (22E)-olefin compound (VII) to afford a triol compound of formula (VIII)

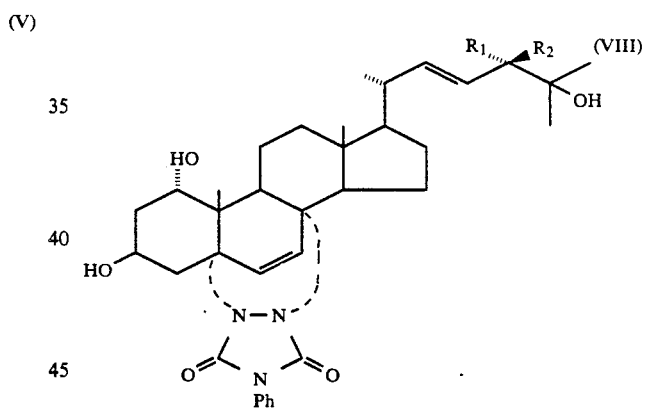

and reducing the triol compound (VIII) to remove the protecting group in the 5,7-diene.

* * * * *